US009058652B2

(12) United States Patent
Hanebuchi et al.

(10) Patent No.: US 9,058,652 B2
(45) Date of Patent: Jun. 16, 2015

(54) METHOD FOR REDUCING NOISE IN TOMOGRAPHIC IMAGE AND RECORDING MEDIUM HAVING NOISE REDUCING PROGRAM STORED THEREIN

(71) Applicant: NIDEK CO., LTD., Gamagori-shi, Aichi (JP)

(72) Inventors: Masaaki Hanebuchi, Aichi (JP); Norimasa Satake, Aichi (JP); Yasuhiro Furuuchi, Aichi (JP); Hajime Namiki, Aichi (JP)

(73) Assignee: NIDEK CO., LTD., Aichi (JP)

( * ) Notice: Subject to any disclaimer, the term of this patent is extended or adjusted under 35 U.S.C. 154(b) by 158 days.

(21) Appl. No.: 13/754,565

(22) Filed: Jan. 30, 2013

(65) Prior Publication Data
US 2013/0208968 A1 Aug. 15, 2013

(30) Foreign Application Priority Data

Jan. 31, 2012 (JP) ................. 2012-019305

(51) Int. Cl.
*G06T 5/00* (2006.01)
*G01B 9/02* (2006.01)
*A61B 3/10* (2006.01)
*A61B 5/00* (2006.01)
*A61B 3/12* (2006.01)

(52) U.S. Cl.
CPC ............ *G06T 5/002* (2013.01); *G01B 9/02004* (2013.01); *G01B 9/0207* (2013.01); *G01B 9/02091* (2013.01); *A61B 3/102* (2013.01); *A61B 3/1225* (2013.01); *A61B 5/0066* (2013.01); *A61B 5/7203* (2013.01)

(58) Field of Classification Search
CPC .... A61B 3/102; A61B 5/0066; A61B 5/7239; G01B 9/02004; G01B 9/0203; G01B 9/02044; G01B 9/02083; G01B 9/02091
USPC ......................................................... 382/128
See application file for complete search history.

(56) References Cited

U.S. PATENT DOCUMENTS

| 7,355,716 B2 * | 4/2008 | de Boer et al. ............... 356/479 |
| 8,558,998 B2 * | 10/2013 | Feldkhun et al. ............. 356/217 |
| 2003/0107743 A1 | 6/2003 | Van Wiggeren |
| 2006/0087616 A1 * | 4/2006 | Hanebuchi .................... 351/210 |
| 2011/0228221 A1 | 9/2011 | Hanebuchi et al. |
| 2011/0299091 A1 | 12/2011 | Yun et al. |

FOREIGN PATENT DOCUMENTS

| JP | 2007-510143 A | 4/2007 |
| JP | 2008272256 A | 11/2008 |
| WO | 2005047813 A1 | 5/2005 |

OTHER PUBLICATIONS

Extended European Search Report issued Jun. 7, 2013 corresponds to EP Patent application No. 13153500.7.

\* cited by examiner

*Primary Examiner* — Tom Y Lu
(74) *Attorney, Agent, or Firm* — Rankin, Hill & Clark LLP

(57) ABSTRACT

A method for reducing noise in a tomographic image, includes: acquiring phase information of a noise component signal, the signal being provided as a signal corresponding to a noise component of the tomographic image and included in a spectrum interference signal output from a detector of a swept source optical coherence tomography device; acquiring a tomographic image in response to a spectrum interference signal with a corrected phase deviation based on the acquired phase information; and reducing the noise component of this tomographic image.

16 Claims, 5 Drawing Sheets

METHOD FOR REDUCING NOISE IN TOMOGRAPHIC IMAGE AND RECORDING MEDIUM HAVING NOISE REDUCING PROGRAM STORED THEREIN

CROSS-REFERENCE TO RELATED APPLICATION

This application is based on Japanese Patent Application No. 2012-019305 filed with the Japan Patent Office on Jan. 31, 2012, the entire content of which is hereby incorporated by reference.

BACKGROUND

1. Technical Field

The present disclosure relates to a method for reducing noise in a tomographic image acquired by a swept source optical coherence tomography device.

2. Related Art

An optical coherence tomography device (Optical Coherence Tomography: OCT) having an optical interference system and capturing a tomographic image of an object has been known. The optical interference optical system of the device splits a light flux emitted from a light source into a measurement light flux and a reference light flux. The optical interference optical system leads the measurement light flux to the object while leading the reference light flux to a reference optical system. Afterward the optical interference optical system obtains interference light by combining the measurement light flux, which are reflected by the object, and the reference light flux. Furthermore, the optical interference optical system causes a light receiving device to receive the interference light. Such a device is used to obtain a tomographic image (OCT image) of a living organism such as an eyeball or skin.

When a tomographic image of an object is captured by the optical coherence tomography device, noise may occur. An interference signal of the noise is displayed as FPN (Fix Pattern Noise) on the tomographic image. Such noise occurs uniformly on each A-scan line (A-scan).

Hence, when a tomographic image is displayed, the FPN of the tomographic image is reduced, for example, by a noise reduction process (e.g., DC subtraction). In the DC subtraction, the average of a spectrum interference signal (raw data) at each scan position is calculated. Furthermore, an average spectrum corresponding to noise is extracted. The average spectrum corresponding to the noise is subsequently subtracted from the spectrum interference signal (raw data). Consequently, FPN (a signal component unrelated to an interference component) is reduced. As a result, an interference signal related to interference light of the reference light and the measurement light is extracted.

The optical coherence tomography device includes, for example, SS-OCT (Swept Source-OCT) (refer to JP-T-2007-510143). In this device, a wavelength variable light source, which temporally changes an emission wavelength at high speed, is used as a light source. SS-OCT can capture an image at higher speed than known SD-OCT (Spectral Domain-OCT).

SUMMARY

A method for reducing noise in a tomographic image, includes: acquiring phase information of a noise component signal, the signal being provided as a signal corresponding to a noise component of the tomographic image and included in a spectrum interference signal output from a detector of a swept source optical coherence tomography device; acquiring a tomographic image in response to a spectrum interference signal with a corrected phase deviation based on the acquired phase information; and reducing the noise component of this tomographic image.

DETAILED DESCRIPTION

Figure 1:
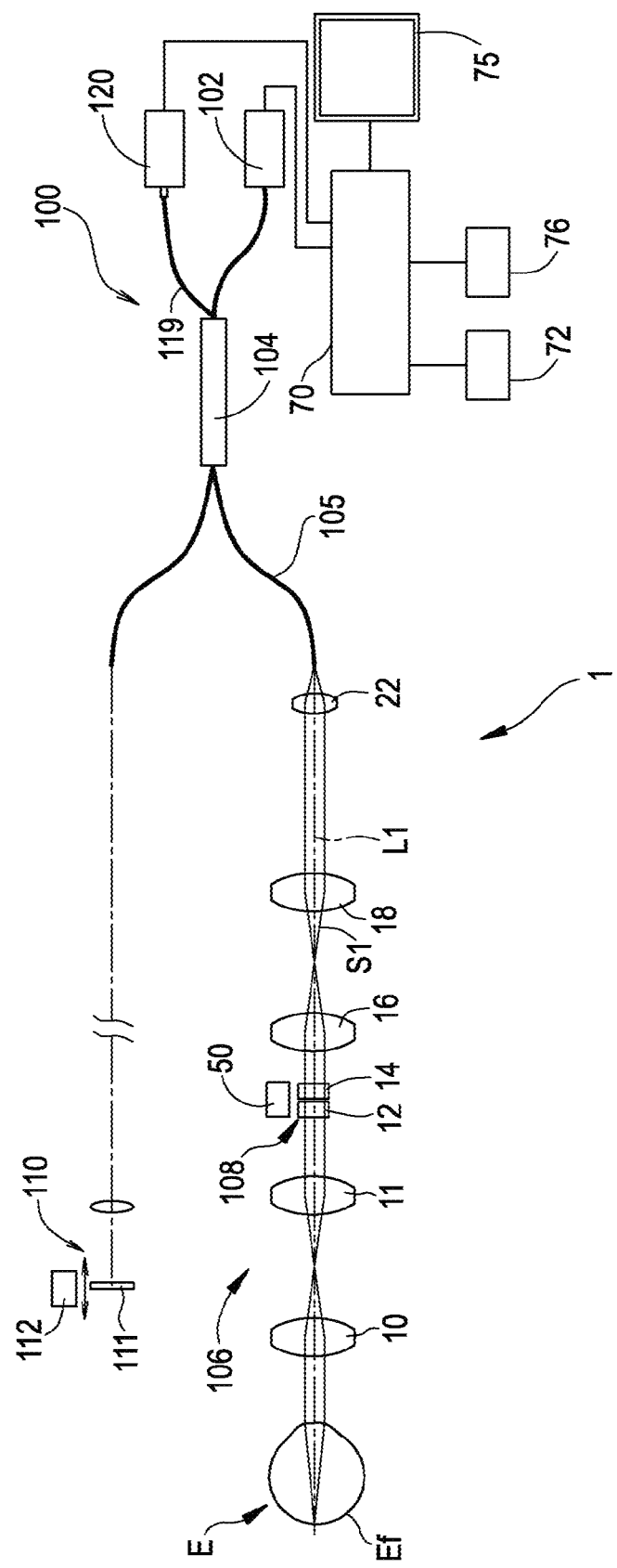
FIG. 1 is a schematic block diagram illustrating the configuration of an optical coherence tomography device according to an embodiment.

In the following detailed description, for purpose of explanation, numerous specific details are set forth in order to provide a thorough understanding of the disclosed embodiments. It will be apparent, however, that one or more embodiments may be practiced without these specific details. In other instances, well-known structures and devices are schematically shown in order to simplify the drawing.

Figure 2:
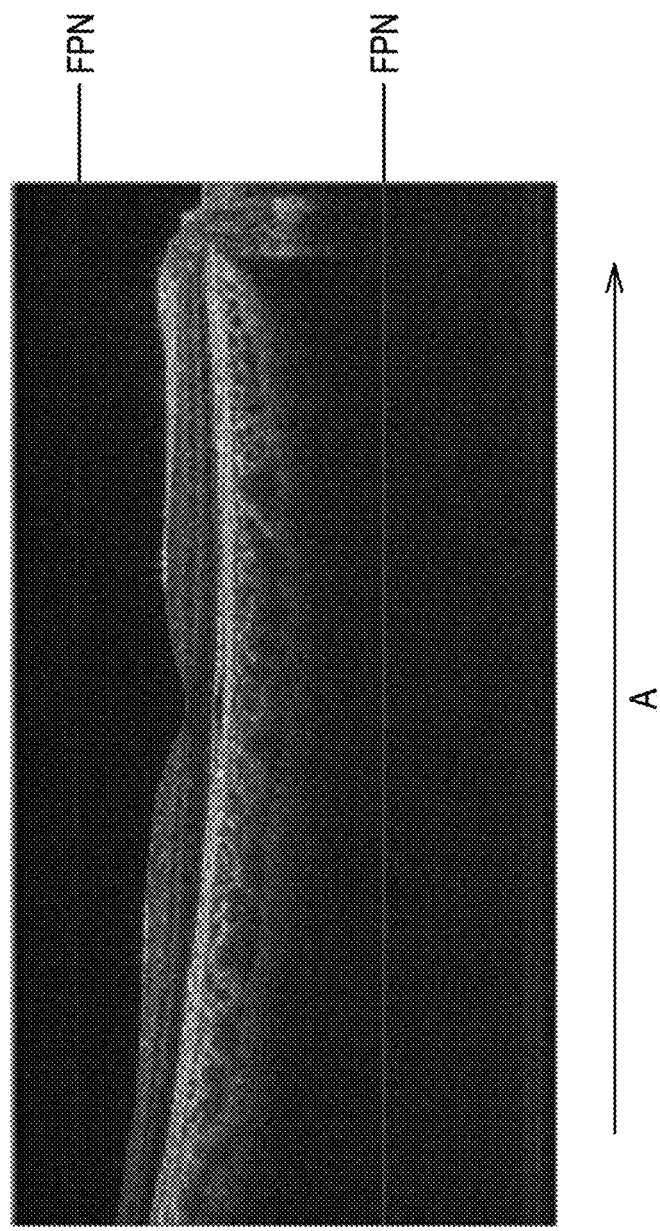
FIG. 2 illustrates an example of occurrence of FPN at a predetermined position of a tomographic image acquired by a wavelength variable light source.

In SS-OCT, even if known noise reduction is performed, noise may appear on a tomographic image (refer to FIG. 2).

One of the causes is described. A wavelength variable light source emits light while changing the wavelength at high speed. Hence, the control of the wavelength variable light source becomes very complicated. Hence, a difference (fluctuation) between the output of a trigger signal for emitting light from the wavelength variable light source and the timing to emit light occurs. The fluctuation shifts the phase of the FPN on each A-scan line (A-scan). Hence, it is conceivable that noise remains.

An object of the present disclosure is to provide an optical coherence tomography device that can acquire a tomographic image where noise has suitably been removed or reduced.

A method for reducing noise in a tomographic image, includes: acquiring phase information of a noise component signal, the signal being provided as a signal corresponding to a noise component of the tomographic image and included in a spectrum interference signal output from a detector of a swept source optical coherence tomography device; acquiring a tomographic image in response to a spectrum interference signal with a corrected phase deviation based on the acquired phase information; and reducing (or removing) the noise component of this tomographic image.

According to this method, it is possible to acquire a tomographic image where noise has suitably been reduced or removed.

A description will be given of an optical coherence tomography device (OCT device) according to an embodiment based on the drawings.

<Outline>

FIG. 1 is a schematic block diagram illustrating the configuration of an optical coherence tomography device 1 according to the embodiment. Firstly, a description will be given of the outline of the optical coherence tomography device 1. As illustrated in FIG. 1, the optical coherence tomography device 1 includes a wavelength variable light source 102, a light splitter (coupler) 104, a scanning optical system (optical scanner) 108, a detector 120, and a calculation control part 70. The calculation control part 70 is used, for example, as an arithmetic processor.

The wavelength variable light source 102 changes the wavelength of an emission light temporally at high speed. The coupler 104 splits the light emitted from the wavelength variable light source 102 into measurement light and reference light. The optical scanner 108 scans an object with the measurement light. The detector 120 receives the spectrum of combined light (spectrum interference signal light). The combined light is obtained by combining the reflected light obtained by the measurement light being reflected by the object, and the reference light. The detector 120 generates and outputs a spectrum interference signal (spectrum signal) in response to the received spectrum interference signal light.

The spectrum interference signal includes a phase deviation. The phase deviation is caused, for example, by a difference in the wavelength variable light source 102's timing to emit light. The control part 70 corrects the phase deviation, and generates a tomographic image in response to the corrected spectrum interference signal. In other words, the control part 70 processes (e.g., performs a Fourier transform on) the spectrum interference signal output from the detector 120 to acquire a first tomographic image. The control part 70 then acquires the phase information of a part (a noise component signal) of the spectrum interference signal, the part corresponding to a noise component remaining in the first tomographic image (OCT image). The control part 70 acquires the phase deviation of the spectrum interference signal based on the phase information of the noise component signal. The control part 70 acquires a second tomographic image in response to a spectrum interference signal with a corrected phase deviation.

In order to obtain the phase information of a noise component signal, the control part 70 obtains the depth position of the noise component in the first tomographic image, for example, by processing the first tomographic image. Consequently, the phase information of the noise component signal, which corresponds to the obtained depth position, is obtained. For example, the control part 70 calculates the average of luminance distribution of each A-scan signal, which forms the first tomographic image, to obtain the depth position of the noise component. Consequently, the depth position of the noise component in the first tomographic image is determined.

In correction of the phase deviation of the spectrum interference signal, for example, the phase deviation of a spectrum interference signal acquired at a predetermined frame rate is corrected based on the phase information of the noise component signal.

For example, the control part 70 reduces the noise component of a spectrum interference signal with a corrected phase deviation (corrected spectrum interference signal), for example. Consequently, the control part 70 extracts the spectrum interference signal having low noise. The control part 70 acquires a second tomographic image (OCT image) based on the spectrum interference signal having low noise. Upon reduction of a noise component, the control part 70 calculates the average spectrum of the spectrum interference signal with a corrected phase deviation (or the average spectrum included in the Fourier transform value), at each scan position. The control part 70 subtracts the average spectrum from the spectrum interference signal with a corrected phase deviation (or a spectrum included in the Fourier transform value), at each scan position. Consequently, a spectrum interference signal having low noise (or the Fourier transform value) is extracted.

For example, there may be a plurality of noise components on the first tomographic image. In this case, a plurality of noise component signals exists in a spectrum interference signal. The control part 70 sequentially uses noise component signals in ascending order of frequency to correct the phase deviation of the spectrum interference signal (tomographic image).

A description will be given of the optical coherence tomography device 1 in more detail.

As illustrated in FIG. 1, the optical coherence tomography (OCT) device 1 includes an interference optical system (OCT optical system) 100, the calculation control unit (CPU) 70, a memory 72, and a monitor 75. In addition, the OCT device 1 includes a front image observing system and a fixation target projecting system (both not shown).

The OCT optical system 100 is an optical system of an SS-OCT (Swept Source-OCT) system. The OCT optical system 100 includes the light source 102, the detector 120, the coupler (splitter) 104, an optical fiber 119, a measuring optical system 106, and a reference optical system 110.

The light source 102 is a wavelength variable light source (wavelength scanning light source). The light source 102 changes the wavelength of emission light temporally at high speed. The detector 120 is, for example, a balanced detector (Balanced Detector) including a light receiving device. The light receiving device of the detector 120 is, for example, a point sensor including one light receiving part. The light receiving part is, for example, an avalanche photodiode.

The light source 102 includes, for example, a laser medium, a resonator, and a wavelength selective filter. The wavelength selective filter of the light source 102 may be, for example, a filter using the combination of a diffraction grating and a polygon mirror, or a Fabry-Perot etalon.

The light source 102 may be a light source whose instantaneous emission line width is short, and resonator length is short. The light source 102 may be a TUNABLE LASER (e.g., $\lambda c=1060$ nm, $\Delta\lambda=110$ nm, $\delta\lambda=0.055$ nm, resonator length~14 mm) manufactured by Axsun Technologies Inc. Such a wavelength variable light source is disclosed, for example, in U.S. Patent Application Publication No. 2009/0059971.

The coupler (splitter) 104 splits light emitted from the light source 102 into measurement light and reference light.

The measuring optical system 106 leads the measurement light to a fundus Ef of an eye E while leading the reference light to the reference optical system 110. The detector (light receiving device) 120 receives interference light acquired by combining the measurement light reflected by the fundus Ef and the reference light.

The measuring optical system 106 includes an optical fiber 105, a collimator lens 22, a focus lens 18, a collimator lens 16, the optical scanner 108, a relay lens 11, and an objective lens 10. They are arranged in this order on an optical path. The focus lens 18 is movable in an optical axis direction. The focus lens 18 is used to adjust focus on the object.

The measurement light from the optical fiber 105 is condensed by the focus lens 18, and is then converted by the collimator lens 16 to a parallel beam. The reflection direction of the measurement light is subsequently changed by the optical scanner 108 including galvanometer mirrors 14 and 12. The measurement light deflected by the optical scanner 108 is once condensed by the relay lens 11. The measurement light is subsequently changed by the objective lens 10 to a parallel beam, and enters the eye E and then the fundus Ef.

The optical scanner 108 scans the fundus Ef with the measurement light in an X-Y direction (transverse direction). The optical scanner 108 is arranged at a position that is substantially conjugated with a pupil. The optical scanner 108 includes, for example, the two galvanometer mirrors 12 and 14. The reflection angles of the galvanometer mirrors 12 and 14 are arbitrarily adjusted by a driving mechanism 50.

In this manner, the travel direction of the light flux emitted from the light source 102 is changed by the optical scanner 108. The fundus is scanned with this light flux in an arbitrary direction. The optical scanner 108 may include reflective mirrors (such as a galvanometer mirror, a polygon mirror, and a resonant scanner). Moreover, the optical scanner 108 may include an acousto-optic modulator (AOM) that changes the travel (deflection) direction of light.

The backscattered light (reflected light) that can be obtained by the measurement light being reflected by the fundus Ef travels through the objective lens 10 to the focus lens 18, and returns to the coupler 104 again. In the coupler 104, the reflected light is multiplexed with the reference light to interfere.

The reference optical system 110 generates reference light that is combined with the above reflected light. The reference optical system 110 may be a Michelson system or Mach-Zehnder system. The reference optical system 110 includes, for example, a catoptric system (e.g., a reference mirror). The reference optical system 110 causes the catoptric system to reflect the light from the coupler 104 and accordingly returns the light to the coupler 104 again and leads it to the detector 120. Otherwise, the reference optical system 110 may include a transmission optical system (e.g., an optical fiber). In this case, the reference optical system 110 does not return the light from the coupler 104 but allow the light pass therethrough to lead the light to the detector 120.

In the OCT device 1, at least a part of optical members arranged in the OCT optical system 100 is moved in the optical axis direction to adjust a difference in optical path length between the measurement light and the reference light. For example, the reference optical system 110 moves an optical member (e.g., a reference mirror 111) on a reference optical path. Consequently, the difference in optical path length between the measurement light and the reference light is adjusted. For example, the reference mirror 111 is moved by a driving mechanism 112 in the optical axis direction. A member to change a difference in optical path length may be arranged on a measurement optical path of the measuring optical system 106. In this case, an optical member (e.g., an end of an optical fiber) arranged on the measurement optical path is moved in the optical axis direction.

Interference signal light obtained by combining the measurement light and the reference light is received by the detector 120 via the optical fiber 119. The detector 120 detects the interference signal light. The detector 120 generates and outputs an interference signal in response to the detected interference signal light.

If the emission wavelength is changed by the light source 102, interference signal light corresponding to this is received by the detector 120. The interference signal light is eventually received by the detector 120 as spectrum interference signal light. The detector 120 generates and outputs a spectrum interference signal in response to the detected spectrum interference signal light. The spectrum interference signal output from the detector 120 is captured by the control part 70. The control part 70 generates a depth profile based on this spectrum interference signal.

The control part 70 controls the drive of the optical scanner 108 to scan the fundus Ef with the measurement light in the transverse direction. The control part 70 sequentially arranges a depth profile at each scan position. Consequently, the control part 70 forms the first tomographic image.

At this point, as illustrated in FIG. 2, a noise component originated from the light source (e.g., FPN (Fix Pattern Noise)) appears at a predetermined position of the tomographic image acquired by use of the wavelength variable light source 102. The FPN is detected at a predetermined position of each A-scan tomographic image, which forms the tomographic image. A description will hereinafter be given of a method for reducing FPN.

Figure 3:
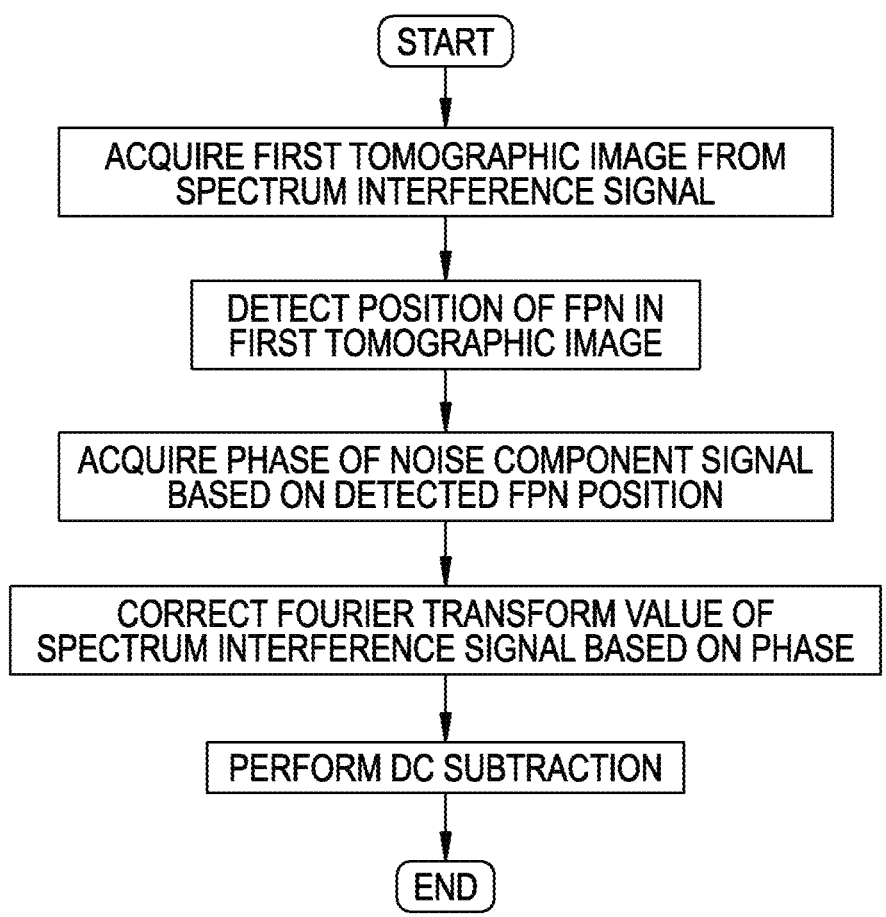
FIG. 3 is a flowchart illustrating an operation procedure of a method for reducing FPN.

FIG. 3 is a flowchart illustrating an operation procedure of a method for reducing the FPN of the first tomographic image in the optical coherence tomography device 1.

Generally, the control part 70 acquires the phase information of a part (a noise component signal) of a spectrum interference signal dependent on the position, where the FPN has been detected, of the first tomographic image. The control part 70 uses the phase information to correct a spectrum interference signal f(k) output from the detector 120. Consequently, the phase deviation (the amount of the phase deviation) of the FPN is corrected. Its example is given below.

The control part 70 controls the drive of the driving mechanism 50 to scan the fundus Ef two-dimensionally with the measurement light. The detector 120 detects spectrum interference signal light related to each scan position (X, Y). The detector 120 outputs the spectrum interference signal f(k). k is a wave number. The wave number k is the reciprocal of the wavelength that can be temporally changed by the light source 102. The spectrum interference signal f(k) is a function of the horizontal axis (wave number k) and the vertical axis (signal strength), and is a signal in the wave number k space.

Firstly, the control part 70 performs a Fourier transform on the spectrum interference signal f(k). Consequently, the control part 70 acquires an A-scan signal (depth profile). The control part 70 arranges the A-scan signals obtained at the scan positions to acquire the first tomographic image.

In other words, the control part 70 performs a Fourier transform process (FFT) on the spectrum interference signal f(k) output from the detector 120. Consequently, the control part 70 acquires a Fourier transform value F(f(k))(Z). The Fourier transform value F(f(k))(Z) includes a real component and an imaginary component. F(f(k))(Z) can also be expressed as F(Z) (a depth profile). The control part 70 obtains the absolute values of the real component and the imaginary component in the Fourier transform value F(f(k))(Z). Consequently, the control part 70 obtains an A-scan signal. The A-scan signal is a function of the horizontal axis (depth position Z) and the vertical axis (signal strength), and indicates signal strength (luminance) in Z space dependent on the depth.

The Fourier transform value F(f(k))(Z) is defined as the following Equation 1.

$$f(k) \xrightarrow{FFT} F(f(k))(Z) = F(Z) = \int_{-\infty}^{\infty} f(k)e^{ikZ}dk \qquad \text{[Equation 1]}$$

The control part 70 detects a position, where the FPN is occurring, in the first tomographic image (a coordinate position in the Z direction). For example, the control part 70 detects the luminance level of the first tomographic image. The control part 70 detects a position of a part having predetermined luminance corresponding to the FPN. At this point, the control part 70 adds the luminance values of A-scan signals in the tomographic image in the scan direction (refer to an arrow A), for example.

The FPN is displayed at a substantially fixed luminance value at a Z position that is substantially fixed. Therefore, as illustrated in FIG. 2, a line extending in the scan direction is normally formed. On the other hand, the luminance value of a fundus tomographic image is different dependent on the portion. Hence, the control part 70 determines the part of the first tomographic image (the part in the Z direction), in which the addition process result in the scan direction results in a predetermined luminance value, as FPN. The FPN is displayed in an area of a fixed limit. Hence, the luminance value may be calculated in advance in the area where the FPN is displayed as in the above to determine the position of the FPN.

The method for determining the position of the FPN is not limited to the above method. The rising edge of strong luminance corresponding to the FPN, a difference between the FPN and a retinal tomographic image (the order of layers anatomically known or a distance from the retinal surface), or the like may be used.

The control part 70 stores the detected position of the FPN in the memory 72. For example, if the FPN is detected at a position (depth position) of a line Z0 in the first tomographic image, the control part 70 stores Z0 in the memory 72 as the position of the FPN. In the first tomographic image, as the position in the Z direction (depth position) becomes deeper, the frequency of the interference signal f(k) corresponding to the position becomes higher.

Next, the control part 70 detects a phase φ(Z0) of a part (a noise component signal), corresponding to the FPN detected position, of the spectrum interference signal based on F(Z0) at the depth position where the FPN has been detected (the FPN detected position), Z0. The phase φ is the phase information of the noise component signal. The phase φ(Z0) is a function of the horizontal axis (wave number k) and the vertical axis (phase (φ). For example, the phase φ(Z0) is obtained from an Arc Tangent (arc tangent) of the ratio of a real part RealF(Z0) and an imaginary part ImagF(Z0) of a Fourier transform value F(Z0) at the FPN detected position Z0. With this Arc Tangent process, the arc tangent of the ratio of the real part and the imaginary part of the Fourier transform value is calculated. As a result, as indicated by the following Equation 2, the phase φ is obtained.

$$\phi = \tan^{-1}\left[\frac{F_{imag}(Z0)}{F_{real}(Z0)}\right] \quad \text{[Equation 2]}$$

Next, the control part 70 corrects the Fourier transform value F(Z) obtained by each A-scan, based on the phase φ of the spectrum interference signal (that is, the phase of the noise component signal) at the acquired FPN detected position Z0. Consequently, the control part 70 removes or reduces the phase deviation (displacement amount) of the spectrum interference signal f(k).

Figure 4:
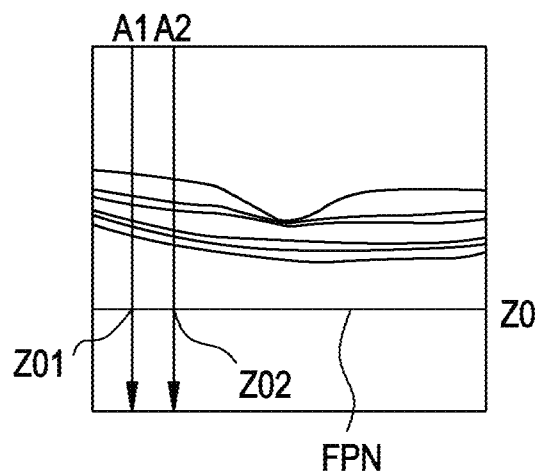
FIG. 4 is a diagram illustrating a method for correcting a phase deviation based on the phase of FPN on A-scans.

The control part 70 corrects a Fourier transform value obtained by each A-scan. Consequently, the control part 70 corrects the phase deviation of a spectrum interference signal obtained by each A-scan. In other words, the control part 70 acquires the phase of a spectrum interference signal (the phase of a noise component signal) at the FPN detected position Z0 for each A-scan. Based on the acquired phase, the Fourier transform value of each A-scan is corrected. For example, as illustrated in FIG. 4, with respect to a first A-scan A1, the Fourier transform value is corrected based on the phase of a spectrum interference signal at an FPN detected position (Z01) on the A-scan A1. Moreover, with respect to a second A-scan A2, the Fourier transform value is corrected based on the phase of a spectrum interference signal at an FPN detected position (Z02) on the A-scan A2.

If a phase deviation is occurring, the spectrum interference signal f(k) is f(k−Δk). Therefore, the Fourier transform value is expressed as the following Equation 3. In Equation 3, k'=k−Δk. Δk is a phase deviation component caused by the fluctuation of an emission timing of the wavelength variable light source 102.

$$\int_{-\infty}^{\infty} f(k-\Delta k)e^{ikZ}dk = \int_{-\infty}^{\infty} f(k')e^{i(k'+\Delta k)Z}dk' \quad \text{[Equation 3]}$$
$$= e^{i\Delta kZ}\int_{-\infty}^{\infty} f(k')e^{ik'Z}dk'$$
$$= e^{i\Delta kZ} \times F(Z)$$

As indicated in Equation 3, if a phase deviation is occurring, the Fourier transform value F(Z) is one where $e^{i\Delta kz}$ is multiplied by the Fourier transform value F(Z) of when there is no phase deviation. Hence, the control part 70 shifts the wave number by Δk in k space by a calculation to remove $e^{i\Delta kz}$ in Z space based on the phase φ. The Fourier transform value F(Z) is F(f(k))(Z), and is a function including the spectrum interference signal f(k). Hence, from the above calculation, the phase of the spectrum interference signal is shifted (corrected) in Z space.

The control part 70 uses the phase φ(Z0) at the FPN detected position Z0 to correct the Fourier transform value F(Z) by the following Equation 4. The phase deviation of a part of the spectrum interference signal, the part corresponding to each Z position that forms the Fourier transform value F(Z) (the phase deviation in the frequency domain), is corrected by this correction process.

$$\exp(-iZ\phi(Z0)/Z0) \times F(Z) \quad \text{[Equation 4]}$$

As described above, the Fourier transform value F(Z) of each A-scan is corrected by the above arithmetic expression. Consequently, the control part 70 acquires a Fourier transform value in response to a spectrum interference signal with a corrected phase deviation.

The control part 70 subsequently performs DC subtraction for reducing the FPN. In the DC subtraction, the control part 70 calculates the average of the raw data of a spectrum interference signal at each scan position (average spectrum). The average spectrum corresponds to noise. The control part 70 may subsequently subtract the average spectrum from the raw data of the spectrum interference signal.

Moreover, the control part 70 can perform the following DC subtraction, for example. The real part spectrum Real f(k) and the imaginary part Imag spectrum f(k) are included in the Fourier transform value F(f(k)) of the spectrum interference signal. The control part 70 obtains the average spectrum of the real part spectrum Real f(k) (a real part average spectrum) and the average spectrum of the imaginary part Imag spectrum f(k) (an imaginary part average spectrum). The control part 70 then subtracts the real part average spectrum from the real part spectrum Real f(k). Furthermore, the control part 70 subtracts the imaginary part average spectrum from the imaginary part Imag spectrum f(k).

The phase of a noise component signal included in a spectrum interference signal agrees regardless of the scan position. Hence, the average spectrum includes the entire FPN.

Hence, from the above calculation, the component, which is caused by the FPN (the signal component unrelated to an interference component), of the Fourier transform value is reduced. As a result, the Fourier transform value F(f(k)) of the spectrum interference signal having low noise in response to the combined light of the reference light and the measurement light is extracted.

The control part 70 obtains the absolute value of the real component and the absolute value of the imaginary component in the Fourier transform value F(f(k)) of the spectrum interference signal having low noise. Consequently, the control part 70 obtains an A-scan signal f(z) at each scan position. The control part 70 arranges the A-scan signals f(z) relative to the scan direction to acquire the second tomographic image.

As described above, it becomes possible to obtain the second tomographic image where the FPN has been reduced, by using the information of the FPN formed on the first tomographic image.

In the above method, the control part 70 performs a Fourier transform on a spectrum interference signal, and then corrects the phase of the spectrum interference signal in Z space. However, it is not limited to this, but the phase of the spectrum interference signal may be corrected in k space before the Fourier transform. Moreover, the order of a noise reduction process such as DC subtraction, and a Fourier transform FFT can be replaced.

A specific description will hereinafter be given of control operations in the optical coherence tomography device 1. The control part 70 controls the driving mechanism 50 to scan the fundus Ef two-dimensionally with the measurement light. The control part 70 then forms the first tomographic image based on the spectrum interference signal f(k) at each scan position.

Figure 5:
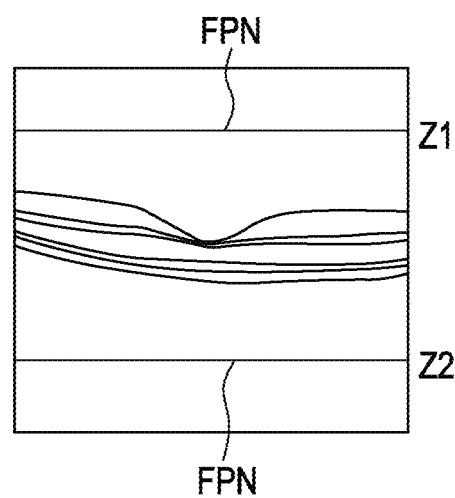
FIG. 5 illustrates an example of the acquired tomographic image.

FIG. 5 is a view illustrating an example of the acquired first tomographic image. The control part 70 detects the luminance level of the first tomographic image. The control part 70 determines positions Z1 and Z2 of the FPN in the first tomographic image, from the detection result of the luminance level. If the control part 70 detects the existence of low-frequency FPN at a position (depth position) of a line Z1 in the first tomographic image, and the existence of high-frequency FPN at a position of a line Z2, the control part 70 stores, in the memory 72, the positions of the lines Z1 and Z2 as the detected positions of the FPN.

Figure 6A:
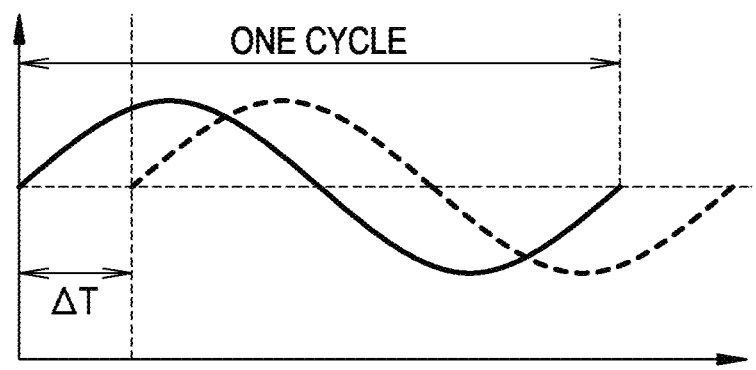
FIGS. 6A and 6B illustrate a phase deviation dependent on frequency.
Figure 6B:
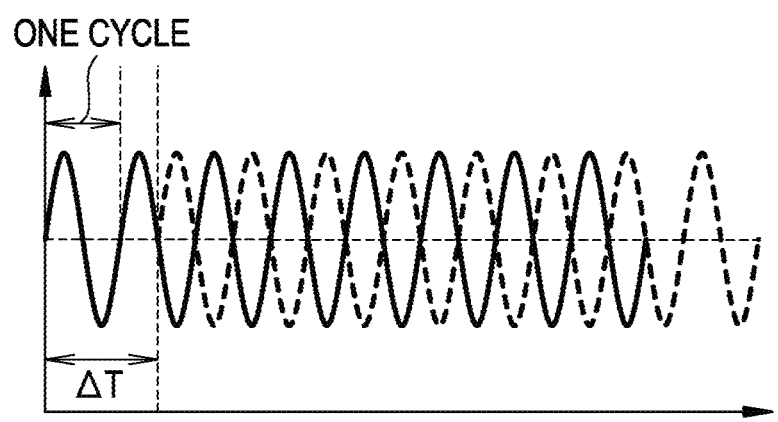

Firstly, the control part 70 corrects the phase deviation of a spectrum signal based on the low-frequency FPN. FIG. 6A illustrates the phase deviation of a low-frequency spectrum interference signal. FIG. 6B illustrates the phase deviation of a high-frequency spectrum interference signal. Assume that a predetermined time lag ΔT occurs in low and high-frequency spectrum interference signals. In this case, the width of one cycle is large in the low-frequency spectrum interference signal; accordingly, the phase deviation is small. Moreover, the width of one cycle is small in the high-frequency spectrum interference signal; accordingly, even if the time lag is slight, the phase deviation is large. In other words, if a predetermined time lag occurs, the phase deviation of low frequency is smaller than the phase deviation of high frequency.

This influences the phase deviation correction of a spectrum interference signal. For example, the phase deviation of a low-frequency spectrum interference signal is coarse and small since the cycle of the spectrum interference signal is large. Consequently, a coarse phase deviation is detected in the low-frequency spectrum interference signal. The control part 70 performs a correction process corresponding to this. On the other hand, the phase deviation of a high-frequency spectrum interference signal is fine and large since the cycle of the spectrum interference signal is small. Consequently, a fine phase deviation is detected in the high-frequency spectrum interference signal. The control part 70 performs a minute correction process to correct the phase deviation.

More specifically, if the phase deviation of a spectrum interference signal is corrected based only on low-frequency FPN, it is difficult to detect the phase deviation since the cycle of the FPN is large. Therefore, the phase deviation of a high-frequency spectrum interference signal may not be able to be reduced only by this correction. Moreover, if the phase deviation of a spectrum interference signal is corrected based only on high-frequency FPN, it is unclear that, for example, the detected phase deviation is a deviation on the same cycle, or one deviated by one or more cycles. Hence, it is difficult to determine how much phase deviation is occurring. Hence, the phase deviation may not be able to be corrected accurately.

The same shall apply to a case where a phase deviation is corrected based on high-frequency FPN, and then a phase deviation is corrected based on low-frequency FPN. In other words, if a phase deviation is corrected based on high-frequency FPN, it becomes unknown that how much phase deviation is occurring. Hence, a subsequent phase deviation may not be able to be corrected accurately.

Hence, the control part 70 corrects a phase deviation based on low-frequency FPN and then corrects a phase deviation based on high-frequency FPN. If doing so, a rough phase deviation of a spectrum interference signal is corrected by the correction based on the low-frequency FPN. With this correction, only a phase deviation of a small cycle remains in the spectrum interference signal. Such a phase shift can be readily detected also by correction based on the high-frequency FPN. As a result, it is possible to ensure the correction of the phase deviation of a spectrum interference signal. In other words, if a plurality of FPN exists in a spectrum interference signal, it is advantageous to use the FPN in ascending order of frequency for the correction of the phase deviation.

For example, the control part 70 detects phase information in low-frequency FPNZ1 (refer to FIG. 5), and corrects the phase deviation of a spectrum interference signal of each A-scan based on the phase information. The control part 70 subsequently detects phase information in high-frequency FPNZ2, and corrects the phase deviation of a spectrum interference signal of each A-scan based on the phase information. The control part 70 subsequently reduces the FPN by DC subtraction.

As described above, the control part 70 can reduce low- and high-frequency FPN readily without changing the optical system. Consequently, the control part 70 can readily acquire a suitable second tomographic image.

If a plurality of FPN exists, the control part 70 may correct the phase deviation of a spectrum interference signal based on predetermined FPN. For example, if a plurality of low-frequency FPN exists, the control part 70 does not need to correct the phase deviations based on all the FPN. The control part 70 can correct also the phase deviation of another FPN by correcting the phase deviation based on a predetermined number of (e.g., one) FPN.

The fundus tomographic image and the FPN are displayed at different positions in the examples illustrated in FIGS. 2 and 5. However, noise reduction by the control part 70 can be carried out, for example, even if the fundus tomographic image overlaps with the FPN in the first tomographic image. In this case, the control part 70 adds luminance values in the Y direction along each Z line of the first tomographic image. A luminance value at a position where the FPN is being displayed is higher than a luminance value at a position where the tomographic image is being displayed. Hence, the control part 70 can detect the position of the FPN. After the FPN is detected, the control part 70 corrects the phase deviation by the above method to reduce the FPN.

In the embodiment, the control part 70 detects FPN in the first tomographic image including the fundus tomographic image to reduce the FPN. However, the control part 70 may obtain the forming position of the FPN using a captured image before the fundus tomographic image is displayed, and detect the forming position of the FPN from the result. The control part 70 may then acquire the phase of the FPN or correct the phase deviation based on the detection result.

In the optical coherence tomography device 1, the phase deviation of a spectrum interference signal can be corrected. Hence, a Doppler OCT image (Doppler tomographic image) can be acquired by obtaining a difference in the phases of spectrum interference signals related to adjacent A-scans.

In the embodiment, a shooting target (object) is a fundus. However, it is not limited to this, but shooting targets include, for example, living organisms such as an anterior segment, a skin, and a viscus, and specimens other than living organisms.

The method for reducing FPN indicated in the embodiment can be conducted, not limited to in the optical coherence tomography device 1, but in another device. Moreover, for example, software (program) for causing another computer to perform a process to be performed by the control part 7070 of the optical coherence tomography device 1 can be supplied to a system or device via a network or various recording media. In this case, a computer (e.g., CPU or the like) of the system or device reads the program to execute the process.

Moreover, in the embodiment, substantially all the processes in the present device may be controlled by the control part 70. Moreover, a program for performing these processes (a noise reducing program or noise reduction software) may be recorded in a recording medium such as the memory 72. Furthermore, an information processing device (e.g., a computer) that can read the program may be used instead of the control part 70.

In this configuration, an arithmetic unit (CPU or MPU) of the information processing device reads the program recorded in the recording medium and executes the processes. Therefore, it can be said that the program itself realizes the processes.

As the above information processing device, in addition to a general computer (e.g., a workstation or personal computer), a function expansion board or function expansion unit that is attached to a computer can be used.

Moreover, the above program includes program codes (an executable program, an intermediate code program, a source program, and the like) of software that realizes the processes. The program may be used singly or in combination with another program (such as an OS). Moreover, the program may be read from a recording medium, then stored once in memory (such as RAM) in the device, and subsequently read again to be executed.

Moreover, a recording medium in which the program is recorded may be one that can be separated readily from the information processing device, or one that is fixed (attached) to the device. Furthermore, a recording medium may be one that is connected to the device as an external storage device.

A magnetic tape such as a video tape or cassette tape, a magnetic disk such as a floppy (registered trademark) disk, MD, or hard disk, a magneto-optical disk such as an MO, an optical disc such as a CD, DVD or BD, a memory card such as an IC card or optical card, a semiconductor memory such as a Mask ROM, EPROM, EEPROM, flash ROM, or USB memory, or the like can be applied as such a recording medium.

Moreover, a recording medium that is connected to the information processing device via networks (an intranet, the Internet, and the like) can be used. In this case, the information processing device acquires the program by downloading via a network. In other words, the above program may be acquired via a transmission medium (a medium holding the program in flux) such as a network (one that is connected to a wired or wireless channel). It is preferable that a program for download should previously be stored in the information processing device (or in a transmitting side device/receiving side device). Moreover, the above recording medium is a non-transitory (non-transitory) medium.

Moreover, the control part 70 may process a spectrum interference signal output from the detector 120 to acquire the first tomographic image. The control part 70 may acquire the phase information of a spectrum interference signal corresponding to a noise component remaining in the acquired first tomographic image. The control part 70 may correct the phase deviation of the spectrum interference signal based on the acquired phase information, process a spectrum interference signal with a corrected phase deviation, and acquire the second tomographic image. The phase deviation of a spectrum interference signal is caused, for example, by a difference in emission timing of the wavelength variable light source 102.

At this point, for example, if there is a plurality of noise components on the first tomographic image, the control part 70 may sequentially correct phase deviations in ascending order of frequency in the spectrum interference signal.

For example, with respect to the phase information of a spectrum interference signal, the first tomographic image is processed to obtain the depth position of a noise component. Accordingly, the phase information of the spectrum interference signal corresponding to the obtained depth position is obtained. For example, with respect to the determination of the depth position of a noise component, the average of the luminance distribution of each A-scan signal forming the first tomographic image is calculated to determine the noise component in the first tomographic image.

For example, the phase deviation of a spectrum interference signal may be corrected based on phase information acquired for each spectrum interference signal acquired at a predetermined frame rate.

For example, if a spectrum interference signal is processed to acquire the first tomographic image, the second tomographic image may be acquired based on an interference signal extracted from a spectrum interference signal where the noise component has been removed. With respect to the extraction of an interference signal, the interference signal may be extracted by calculating the average spectrum of a spectrum interference signal with a corrected phase deviation at each scan position, and subtracting the average spectrum from the spectrum interference signal at each scan position.

Generally the control part 70 may correct the phase deviation (phase deviation amount) of FPN by acquiring a phase signal of a spectrum interference signal at a FPN detected position, and correcting the interference signal f(k) using the acquired phase signal.

In a fundus tomographic image, there is a difference in luminance value dependent on the portion. Hence, the control part 70 may determine a signal of a part having a predetermined luminance value as FPN, based on a profile obtained by the addition process in the scan direction. The FPN is displayed in a fixed area. Accordingly, the FPN may be determined by presetting a predetermined position to determine the FPN, and detecting a luminance value of the set position or area.

Moreover, the method for removing (that is, reducing) noise of the present disclosure may be the following first to eighth methods for removing noise. The first method for removing noise is a method for removing noise of an OCT image that is acquired by a swept source optical coherence tomography. An OCT image where a noise component has been removed is acquired by: acquiring the phase information of a signal corresponding to a noise component included in a spectrum signal output from a detector of the swept source optical coherence tomography; correcting the phase deviation of the spectrum signal based on the acquired phase information; and processing a spectrum signal with a corrected phase deviation.

In the first method for removing noise, the second method for removing noise processes the OCT image that has been acquired first, obtains the depth position of the noise component, and acquires the phase information of a spectrum signal corresponding to the obtained depth position.

In the first or second method for removing noise, the third method for removing noise acquires phase information for each spectrum signal acquired at a predetermined frame rate, and corrects the phase deviation of the spectrum signal.

In accordance with the fourth method for removing noise in the first method for removing noise, if there is a plurality of noise components on the OCT image acquired first, phase deviations are sequentially corrected in ascending order of frequency in the spectrum signal.

In accordance with the fifth method for removing noise in any one of the first to fourth methods for removing noise, the noise component is FPN (Fix Pattern Noise).

In accordance with the sixth method for removing noise in any one of the first to five methods for removing noise, an interference signal is extracted from a spectrum signal by calculating an average spectrum of a spectrum signal with a corrected phase deviation at each scan position, and subtracting the average spectrum from a spectrum signal at each scan position.

In accordance with the seventh method for removing noise in any one of the first to sixth methods for removing noise, the luminance distribution of an A-scan signal is obtained based on the interference signal extracted from the spectrum signal, and an OCT image is acquired from the obtained luminance distribution at each scan position.

In accordance with the eighth method for removing noise in any one of the first to seventh methods for removing noise, the average of the luminance distribution of each A-scan signal forming the OCT image acquired first is calculated to determine a noise component.

Moreover, a recording medium of the present disclosure may be the following first recording medium. The first recording medium is a recording medium in which a noise removing program of an OCT image acquired by a swept source optical coherence tomography is stored, and the noise removing program is executed by a control part for controlling the operation of the swept source optical coherence tomography to cause the swept source optical coherence tomography to execute: acquiring the phase information of a signal corresponding to a noise component included in a spectrum signal output from a detector of the swept source optical coherence tomography; correcting the phase deviation of the spectrum signal based on the acquired phase information; processing a spectrum signal with a corrected phase deviation; and acquiring an OCT image where the noise component has been removed.

The foregoing detailed description has been presented for the purposes of illustration and description. Many modifications and variations are possible in light of the above teaching. It is not intended to be exhaustive or to limit the subject matter described herein to the precise form disclosed. Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims appended hereto.

What is claimed is:

1. A method for reducing noise in a tomographic image, comprising:
    acquiring a first tomographic image based on a spectrum interference signal output from a detector of a swept source optical coherence tomography device;
    acquiring a phase of a noise component signal, the noise component signal being provided as a signal corresponding to a noise component of the first tomographic image and included in the spectrum interference signal output from the detector of the swept source optical coherence tomography device;
    correcting a phase deviation of the spectrum interference signal based on the acquired phase; and
    reducing the noise component signal in the spectrum interference signal in which the phase deviation has been corrected to acquire a second tomographic image.

2. The method for reducing noise in a tomographic image according to claim 1, wherein the acquiring phase of the noise component signal includes
    acquiring a depth position of the noise component in the first tomographic image, and
    acquiring the phase of the noise component signal corresponding to the depth position of the noise component in the first tomographic image.

3. The method for reducing noise in a tomographic image according to claim 1, wherein the acquiring phase of the noise component signal includes acquiring phase of the noise component signal of each spectrum interference signal acquired at a predetermined frame rate.

4. The method for reducing noise in a tomographic image according to claim 1, wherein, when a plurality of noise components is present in the first tomographic image obtained from the spectrum interference signal output from the detector of the coherence tomography device, the noise component signals are used in ascending order of frequency to correct the phase deviation of the spectrum interference signal.

5. The method for reducing noise in a tomographic image according to claim 1, wherein the noise component is Fix Pattern Noise.

6. The method for reducing noise in a tomographic image according to claim 5, wherein the acquiring phase of the noise component signal includes
    detecting a position of FPN in the first tomographic image; and
    acquiring the phase of the noise component signal based on a Fourier transform value at the position of FPN.

7. The method for reducing noise in a tomographic image according to claim 6, wherein the phase of the noise component signal is acquired from an arc tangent of ratio of a real part and an imaginary part of the Fourier transform value at the position of FPN.

8. The method for reducing noise in a tomographic image according to claim 6, wherein the correcting the phase deviation of the spectrum interference signal includes correcting the Fourier transform value obtained by each A-scan based on the acquired phase of the noise component signal at the position of FPN.

9. The method for reducing noise in a tomographic image according to claim 5, wherein
the acquiring phase of the noise component signal includes
detecting a position of FPN in the first tomographic image; and
acquiring the phase of the noise component signal based on a Fourier transform value at the position of FPN for each A-scan, and
the correcting the phase deviation of the noise component signal includes
correcting the Fourier transform value for each A-scan based on the acquired phase at the position of FPN.

10. The method for reducing noise in a tomographic image according to claim 1, wherein the reducing the noise component signal includes
calculating an average spectrum of the spectrum interference signal in which the phase deviation has been corrected, and
subtracting the average spectrum from the spectrum interference signal at each scan position.

11. The method for reducing noise in a tomographic image according to claim 10, wherein
the reducing the noise component signal includes obtaining an A-scan signal at each scan position based on the spectrum interference signal from which the average spectrum is subtracted, and
the second tomographic image is acquired by arranging the obtained A-scan signals in a scan direction.

12. The method for reducing noise in a tomographic image according to claim 1, wherein the reducing the noise component signal includes
calculating an average spectrum of a Fourier transform value of the spectrum interference signal in which the phase deviation has been corrected, and
subtracting the average spectrum from a spectrum interference signal included in the Fourier transform value at each scan position.

13. The method for reducing noise in a tomographic image according to claim 12, wherein
the reducing the noise component signal includes obtaining an A-scan signal at each scan position based on the Fourier transform value from which the average spectrum is subtracted, and
the second tomographic image is acquired by arranging the obtained A-scan signals in a scan direction.

14. The method for reducing noise in a tomographic image according to claim 1, wherein the acquiring phase of the noise component signal includes
calculating an average of luminance distribution of an A-scan signal forming the first tomographic image.

15. A non-transitory recording medium having a noise reducing program stored therein, the program causing an information processing device to execute the method for reducing noise according to claim 1.

16. A non-transitory recording medium having a noise reducing program stored therein, the program causing a control part for controlling operation of a swept source optical coherence tomography device to execute:
acquiring a first tomographic image based on a spectrum interference signal output from a detector of a swept source optical coherence tomography device;
acquiring a phase of a noise component signal, the noise component signal being provided as a signal corresponding to a noise component of the first tomographic image and included in the spectrum interference signal output from the detector of the swept source optical coherence tomography device;
correcting a phase deviation of the spectrum interference signal based on the acquired phase; and
reducing a noise component signal in the spectrum interference signal in which the phase deviation has been corrected to acquire a second tomographic image.

* * * * *